United States Patent [19]

Stuhmer et al.

[11] Patent Number: 4,795,466
[45] Date of Patent: Jan. 3, 1989

[54] ARTIFICIAL CRUCIAL LIGAMENT FOR A KNEE JOINT

[75] Inventors: Karl-Gerhart Stuhmer, Ravensburg, Fed. Rep. of Germany; Otto Frey, Winterthur; Rudolf Koch, Berlingen, both of Switzerland

[73] Assignee: Sulzer Brothers Limited, Winterthur, Switzerland

[21] Appl. No.: 20,456

[22] Filed: Mar. 2, 1987

[30] Foreign Application Priority Data

Mar. 7, 1986 [CH] Switzerland ............... 954/86

[51] Int. Cl.⁴ ............................................. A61F 2/08
[52] U.S. Cl. .......................................... 623/13; 623/11; 623/66; 128/335.5; 87/9
[58] Field of Search ................ 128/334 R, 335.5; 623/1, 2, 11, 13, 66; 66/169 R, 196; 139/387 R; 87/9, 11, 13

[56] References Cited

U.S. PATENT DOCUMENTS

| | | | |
|---|---|---|---|
| 3,107,189 | 10/1963 | Hill et al. | 623/66 |
| 3,561,318 | 2/1971 | Andriot, Jr. | 87/9 |
| 3,613,120 | 10/1971 | McFarland | 623/13 |
| 3,938,524 | 2/1976 | Sparks et al. | 623/1 X |
| 4,187,558 | 2/1980 | Dahlen et al. | 623/13 X |
| 4,255,820 | 3/1981 | Rothermal et al. | 623/13 |
| 4,501,263 | 2/1985 | Harbuck | 623/1 X |
| 4,584,722 | 4/1986 | Levy et al. | 623/13 |
| 4,642,119 | 2/1987 | Shah | 623/13 |
| 4,662,886 | 5/1987 | Moorse et al. | 623/13 |
| 4,728,329 | 3/1988 | Mansat | 623/11 |

FOREIGN PATENT DOCUMENTS

| | | | |
|---|---|---|---|
| 0653155 | 3/1935 | Fed. Rep. of Germany | 87/9 |
| 2592578 | 7/1987 | France | 623/12 |

Primary Examiner—Richard J. Apley
Assistant Examiner—Paul Prebilic
Attorney, Agent, or Firm—Kenyon & Kenyon

[57] ABSTRACT

The artificial crucial ligament is formed of a plurality of tubes which are disposed in concentric relation to define a stem. Alternating tubes extend from the stem to form two branches. The tubes are made of textile structures to impart flexibility and longitudinal elasticity to the ligament. In one embodiment, the tubes are made of a braided construction.

13 Claims, 1 Drawing Sheet

ARTIFICIAL CRUCIAL LIGAMENT FOR A KNEE JOINT

This invention relates to an artificial crucial ligament for a knee joint.

Heretofore, various types of artificial crucial ligament constructions have been known for use in a knee joint. For example, French Pat. No. 2,213,761 describes an artificial crucial ligament which has a stem and a pair of branches which extend from the stem. As described, the stem of the crucial ligament consists of a plurality of longitudinal monofilament threads, preferably four threads of polyamide while each branch is formed of two threads to define a front crucial ligament and a back crucial ligament, respectively. In addition, the longitudinally disposed threads are described as being enveloped in a fabric sheath of a bio-inert synthetic material while also being connected to the sheath through tissue compatible adhesives or sutures. In order to achieve the necessary tensile strength, the threads have to be of a minimum thickness. However, this impairs the elastic longitudinal extensibility of the ligament. Further, the longitudinally disposed threads would rub continuously against each other in use and would therefore be subject to a relatively high degree of wear.

Similar artificial ligaments of an unbranched type are also known from European Pat. No. 0,126,520 and U.S. Pat. No. 4,255,820 in which a fabric sheath envelopes a stem running in a longitudinal direction or "longitudinal threads".

It is an object of the invention to create an artificial cruciate ligament having a stem and at least two branches wherein the extensability and flexibility of the ligament are considerably improved compared to previously known structures.

It is another object of the invention to improve the longitudinal elasticity of artificial crucial ligaments for knee joints.

It is another object of the invention to provide an artificial crucial ligament having relatively good elasticity chrracteristics to enhance implantation and use.

Briefly, the invention provides an artificial crucial ligament for a knee joint which has a plural of layers of tubular textile structures disposed in concentric relation to define a stem with the layers extending from the stem to define at least a pair of branches.

The term "textile tubular structures" is intended to mean "hollow cylinders" which consist of multifilament threads or monofilaments, for example, wires, and which can be produced by processes such as braiding, weaving and knitting. These structures are characterized as having required minimum values for elastic longitudinal extensibility and flexibility of the ligament. By way of example, the ligaments can be produced by braiding on a braiding machine.

In one embodiment, the ligament is made of braided construction with the individual layers or tubes extending in alternating manner from the stem into the branches. Alternatively, the innermost layers in the stem may extend into one branch while the outermost layers in the stem extend into a second branch. The required longitudinal extensibility and flexibility are achieved during production of the ligament from the braided tubes by setting the braiding angle relative to the axis of the ligament. For example, the flexibility of the braided ligament is greater as the braiding angle is lower relative to the longitudinal axis.

Where the ligament layers are woven or knitted, it is possible to have each individual layer extend from the stem into each of the branches.

The individual layers or tubes can be made of multifil or monofil threads. In this respect, the term "monofil threads" includes metallic wires. The threads may also be of natural fiber, for example silk, or may be of synthetic fibers, for example of polyester, polyethylene or any known reabsorbable material.

In order to produce a ligament, a large number of concentric tubes, for example twenty or thirty are pulled or layered one about the other in a concentric relationship. For braided tubes, twisted threads of a large number, for example sixty monofilaments consisting, for example, of polyester and having a diameter of 0.01 to 0.03 millimeters have proven advantageous.

In order obtain the densest possible braiding and thus achieve increased mechanical strength, the outermost tubes can be formed of an increased number of threads relative to the innermost tubes or may be formed of threads having larger diameters than the innermost threads. For example, the use of monofilaments may be made in the innermost tubes while multifilament threads are used in the outermost tubes. Increasing the density of the outermost tubes also permits a relatively dense and smooth surface to be created.

These and other objects and advantages of the invention will become more apparent from the following detailed description taken in conjunction with the accompany drawings wherein.

Figure 1:
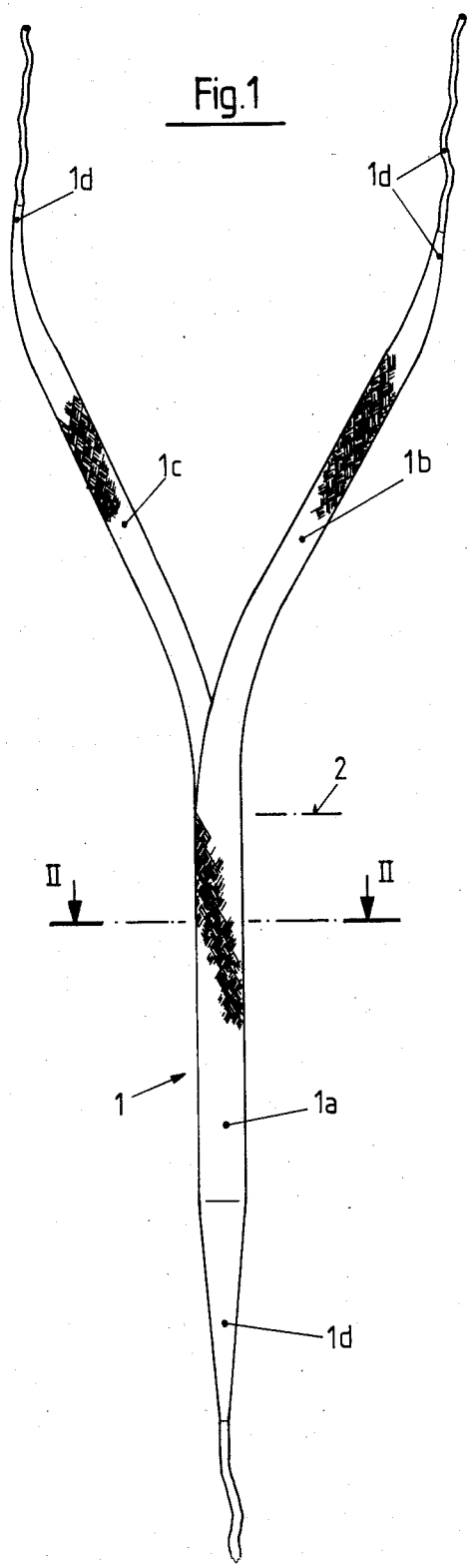
FIG. 1 illustrates a schematic view of an artificial crucial ligament constructed in accordance with the invention.

Referring to FIG. 1, the artificial crucial ligament 1 is constructed for use in a knee joint. To this end, the ligament has a stem 1a and a pair of branches 1b, 1c. In addition, the free end of the stem 1a and the free ends of the branches 1b, 1c may continue as thin threading sections 1d which may be reinforced by inlays or by impregnation with a hardening substance.

Figure 2:
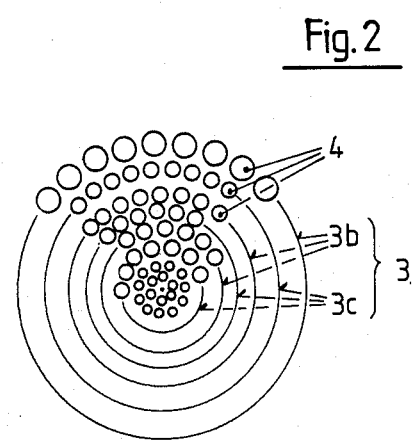
FIG. 2 illustrates a cross sectional view taken on line II—II of FIG. 1.

Referring to FIGS. 1 and 2, the stem 1a is formed of a plurality of concentric layers or tubes of tubular textile structures 3. As indicated in FIG. 2, the individual threads 4 of the concentric layers 3 may be formed of allarge number of monofilaments which are twisted into a multifilament thread (not expressly shown).

In order to obtain a relatively dense and smooth surface of the ligament 1, the threads 4 of the outermost tubes are of larger diameter or thickness than the threads of the innermost tubes. For example, each thread of the outermost tubes can be made by twice as many monofilaments as the threads of the innermost tubes.

As indicated in FIG. 1, the ligament 1 is made of tubes which are of braided construction, for example being produced on a braiding machine. The ligament is constructed so that all of the tubes extend concentrically throughout the stem 1a up to the point 2, as viewed, from which the tubes branch in an alternating manner into the respective branches 1b 1c. In this respect, as indicated in FIG. 2, the tubes 3b form the branch 1b while the alternating tubes 3c form the second branch 1c. Alternatively, it is also possible to form one of the branches from the innermost tubes and the other branch from the outermost tubes of the stem. Still further, with woven or knitted tubes, each tube may be branched from the stem into two branches.

Figure 3:
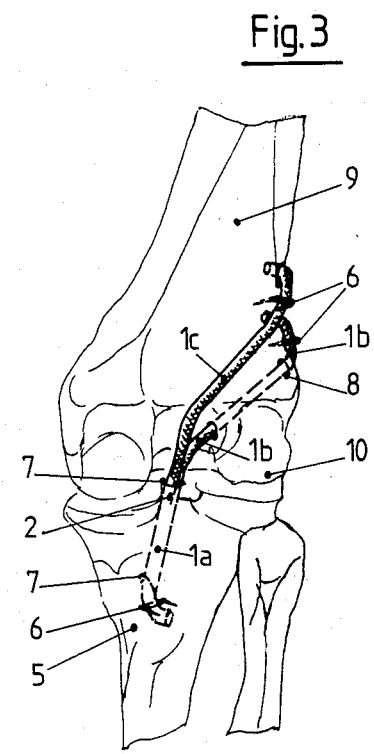
FIG. 3 illustrates a dorsal view of a knee joint in which a crucial according to the invention has been implanted. planted.

Referring to FIG. 3, the implantation techniques to be used with the ligament 1 are very simple. For example, before fastening the stem 1a to a tibia 5, both branches 1b, 1c of the ligament 1 are guided through a bore 7 in the tibia 5. Because of the pull and, as a consequence of the elastic longitudinal elasticity, the diameter of the ligament 1 is decreased and can thus be pulled through the bore 7 without difficulty. Upon cessation of the tensile stress, the ligament 1 swells and thereby comes into intimate contact with the bone in the bore 7 to support tissue growth on and into the ligament stem 1a. The stem 1a is then fixed to the frontal aspect of the tibia 5 with a clip or clasp 6 which is driven into the tibia 5. The end of the ligament 1 is then cut with a sharp cutting tool, for example a scalpel, a few centimeters beyond the clasp 6 and fitted into a previously created pocket bore in the tibia 5.

Of note, the length of the stem 1a relative to the length of the bore 7 in the tibia 5 is selected in such a way that the branching point 2 is located within the bore 7.

After emerging from the bore 7, one of the branches 1c is passed between the condyles, that is over the top of the condyles, and is clamped laterally to the outside of the femur 9 in the same manner as the stem 1a is fastened to the tibia 5. As such, the branch 1c forms a substitute of the dorsal crucial ligament. The other branch 1b is guided through and additional bore 8 which penetrates the femur 9 above the lateral condyle 10 and passes to the lateral outside of the femur 9. This branch 1b is fastened with a clasp 6 in a similar manner as above.

In order to reduce the tensile load on the anchoring site, the "back" crucial ligament, in particular, is guided for a relative long distance to rest on the femur 9 before being anchored. This "long" resting of the ligament on the femur 9 causes increased friction through which a portion of the tensile stress is consumed and kept from the anchoring site at the clasp 6. In similar manner, the anchoring sites of the stem 1a and the branch 1c are protected against excessive stress by the frictional contact between the ligament 1 and the surfaces of the tibia 5 and femur 9 as well as by the surfaces within the bores 7, 8.

As indicated in FIG. 2, the ligament 1 is formed of a relative large number of concentric layers or tubes. As a result, the ligament has an increased flexibility and longitudinal elasticity. Further, as indicated in FIG. 2, the ligament forms a hollow construction and eliminates any core of material which might otherwise impair the longitudinal elasticity o the ligament.

The various tubes of the ligament can be assembled in any suitable manner. Further, where the individual tubes are made of braided construction, the angle of the braid may be adjusted in production to suit the desired degree of elasticity desired for the ligament.

What is claimed is:

1. An artificial crucial ligament for a knee joint, said ligament having a at least three layers of tubular textile structures disposed in concentric relation to define a stem with said layers extending from said stem to define a pair of branches.

2. An artificial crucial ligament as set forth in claim 1 wherein some of said layers extend from said stem to define one of said branches and others of said layers extend from said stem to define a second of said branches.

3. An artificial crucial ligament as set forth in claim 2 wherein said layers extend in alternating manner from said stem into said branches.

4. An artificial crucial ligament as set fort in claim 2 wherein the innermost layers in said stem extend into one of said branches and the outermost layers in said stem extend into the other of said branches.

5. An artificial crucial ligament as set forth in claim 1 wherein each layer extends from said stem into each of said branches.

6. An artificial crucial ligament as set forth in claim 1 wherein said layers define a hollow core.

7. An artificial crucial ligament as set forth in claim 1 wherein each layer is flexible and longitudinally elastic.

8. An artificial crucial ligament as set forth in claim 7 wherein each layer is made of a braided construction.

9. An artificial crucial ligament as set forth in claim 1 wherein each layer is made of threads.

10. An artificial crucial ligament comprising at least three tubular textile structures disposed in concentric relation to define a hollow stem and extending from said stem to define at least a pair of hollow branches, each said structure being flexible and longitudinally elastic.

11. An artificial crucial ligament as set forth in claim 10 wherein each tubular structure is made of threads.

12. An artificial crucial ligament as set forth in claim 11 wherein the outermost structures are made of threads having a greater diameter than the threads of the innermost structures.

13. An artificial crucial ligament as set forth in claim 10 wherein each tubular textile structure is made of braided construction.

* * * * *

UNITED STATES PATENT AND TRADEMARK OFFICE
CERTIFICATE OF CORRECTION

PATENT NO. : 4,795,466

DATED : January 3, 1989

INVENTOR(S) : KARL-GERHART STUHMER, et al

It is certified that error appears in the above-identified patent and that said Letters Patent is hereby corrected as shown below:

```
Column 1, line 42 change "chharacteristics" to -characteristics-
Column 1, line 44 change "plural" to -plurality-
Column 2, lines 29 and 30 change "accompany" to -accompanying-
Column 2, line 50 change "allarge" to -a large-
Column 3, line 32 change "and" to -an-
Column 3, line 50 change "relative" to -relatively-
Column 4, line 11 change "a at least" to -at least-
```

Signed and Sealed this

Thirty-first Day of October, 1989

Attest:

DONALD J. QUIGG

Attesting Officer

Commissioner of Patents and Trademarks